United States Patent [19]

Gerritsen et al.

[11] 4,193,942
[45] Mar. 18, 1980

[54] PROCESS FOR CATALYTIC CONVERSION OF OLEFINICALLY UNSATURATED COMPOUNDS WITH HYDROGEN AND/OR CARBON MONOXIDE

[75] Inventors: Leendert A. Gerritsen, Delft; Joseph J. F. Scholten, Geleen, both of Netherlands

[73] Assignee: Stamicarbon, B.V., Geleen, Netherlands

[21] Appl. No.: 870,582

[22] Filed: Jan. 18, 1978

[30] Foreign Application Priority Data

Jan. 20, 1977 [NL] Netherlands .................... 7700554
Nov. 17, 1977 [NL] Netherlands .................... 7712648

[51] Int. Cl.² ............................................. C07C 45/08
[52] U.S. Cl. ........................... 260/604 HF; 252/431 P
[58] Field of Search ............. 260/604 HF; 252/431 P

[56] References Cited

U.S. PATENT DOCUMENTS

| 3,733,362 | 5/1973 | Biale | 260/604 HF |
|---|---|---|---|
| 3,937,742 | 2/1976 | Yoo | 260/604 HF |
| 3,940,447 | 2/1976 | Yoo | 260/604 HF |
| 3,989,759 | 11/1976 | Yoo | 260/604 HF |

FOREIGN PATENT DOCUMENTS 1185453 4/1970 United Kingdom ............. 260/604 HF

*Primary Examiner*—Werren B. Lone
*Attorney, Agent, or Firm*—Cushman, Darby & Cushman

[57] ABSTRACT

Olefinically unsaturated compounds are subjected to hydroformylation to produce the corresponding aldehyde having an additional carbon atom by reacting the compound with hydrogen and carbon monoxide under appropriate conditions of temperature and pressure in the presence of a catalytically active metallo-organic complex in the pores of a solid porous carrier in the form of a solution in a ligand-forming electron-donating phosphorous compound, such as triethyl phosphine, that has a vapor pressure of less than 15 mbar under reaction conditions. The central atom of the metallo-organic complex is preferably rhodium, cobalt, ruthenium or irridium.

7 Claims, No Drawings

PROCESS FOR CATALYTIC CONVERSION OF OLEFINICALLY UNSATURATED COMPOUNDS WITH HYDROGEN AND/OR CARBON MONOXIDE

BACKGROUND OF THE INVENTION

The invention relates to a process for conversion of an olefinically unsaturated organic compound with hydrogen and/or carbon monoxide in the presence of a catalyst consisting of a particle-shape, solid, porous carrier in the pores of which a catalytically active metallic complex, dissolved in a solvent which is slightly volatile under the reaction conditions, is present.

The invention relates in particular to hydroformylation of unsaturated compounds, which means conversion with carbon monoxide and hydrogen into an aldehyde with one additional carbon atom in the molecule.

It is known for the hydroformylation to be carried out with application of a catalytically active metallo-organic complex. By the term metallo-organic complex is meant a compound consisting of a central metal atom and one or more ligands, the central metal atom being a transition metal, like rhodium, ruthenium or cobalt. By the term ligand is meant an atom, radical, ion or molecule that can be bound to the central metal atom in a polyatom compound, for instance hydrogen, carbon monoxide and triphenylphosphine, in rhodiumhydridocarbonyltris (triphenylphosphine).

Hydroformylation, carbonylation or hydrogenation of unsaturated compounds can be carried out with application of a solution of a catalytically active metallic complex. However, this involves certain problems connected with recovery of the reagents and loss of solvent and metallic complex. It is also possible for the metallic complex to be physically or chemically bound to a solid carrier, so that a heterogeneous catalyst is obtained. In this case, however, the life of the catalyst is still too small for technical application owing to deactivation and rinse-off of the catalytically active complex. The advantages entailed by application of a heterogeneous catalyst can also be achieved by dissolving the catalytically active metallic complex in a solvent which is slightly volatile under the reaction conditions to be applied and by impregnating the pores of a porous, solid carrier with a solution of this kind, see British Patent Specification 1,185,453. These catalysts are sometimes called 'Supported Liquid Phase Catalyst' (SLPC). The solvent may be a hydrocarbon, alcohol, carboxylic acid or an ester. The activity of the known SLPC catalyst is rather low however, while also the selectivity, that means the ratio between the primary and branched aldehydes produced from α-olefins, is only low.

DETAILED DESCRIPTION OF THE INVENTION

According to the invention an olefinically unsaturated organic compound can be converted with hydrogen and/or carbon monoxide at a temperature of 20°-300° C. and a pressure of 1-100 bar in the presence of a catalyst consisting of a solid, porous carrier in the pores of which a catalytically active metallic complex, dissolved in a solvent which is slightly volatile under the reaction conditions, is present, the catalytically active metallic complex being present in the pores of the carrier in the form of a solution in one or more ligand-forming compounds having a vapour pressure of less than 15 mbar under the reaction conditions applied.

It has proved that the activity, the selectivity and the stability of the catalysts applied in the process according to the invention are very favourable. Another advantage is that the process can also be carried out at a temperature below the melting point of the solution of the active metallic complex in the ligant-forming solvent, so that a solid solution is then present in the pores of the carrier material.

For the central metal atom in the catalytically active metallo-organic complex there are to be considered the transition metals from the groups V, VI, VII and VIII of the Periodic System according to Mendelyeev, such as Re, Fe, Ru, Os, Co, Rh, Ir, Ni, Pd and Pt, in particular rhodium, cobalt, ruthenium, and iridium. Said metals can be applied as mixture as well.

For ligands in the above-mentioned metallo-organic complex there are to be considered, ligands like Co, H and σ- and π—bound alkenes, organic compounds which contain in the molecule one or more atoms from the groups VB and VIB of the Periodic System according to Mendelyeev with a free pair of electrons, for instance P, S, B, Se, Te, Sb, As. Also suitable are, for instance, the halides, such as Cl, Br and J, tin- and germanium II-halides, acid radicals like acetate, propionate and easily movable ligands, such as acetylacetonate, hydrogen, carbon monoxide, tetrahydrofuran and diolefin such as e.g. cyclooctadiene.

For complexes special mention may be made of rhodiumhydridocarbonyltris (triphenylphosphine), cobalthydridotetracarbonyl, rhodiumbis (triphenylphosphine) carbonylchloride, rhodiumhydridobiscarbonylbis (triphenylphosphine), rhodiumbis (triphenylarsine) carbonylchloride, rhodium trichloride and complexes consisting of an anionic and a cationic component, such as e.g. $[RH (CO)_3 (PPh_3)_2] [BPh_4]$ and $[Ir (CO)_3 (PPh_3)][PF_6]$.

As solvent for the metallic complex compounds may be applied according to the invention which have a vapour pressure of less than 15 mbar under the reaction conditions, and which are capable to act as ligand in a transition-metal complex. These ligand-forming compounds, hereafter also called 'free ligand', need not be equal to the ligands present in the original transition-metal complex. If necessary, they may replace one or more ligands of the metallic complex. It is even likely that, under operating conditions, the catalytically active metallic complex differs from the metal compound originally brought in solution. For the ligand-forming compounds applied as solvent are to be considered in particular the organic compounds of phosphorus, antimony and arsenic, which contain a free pair of electrons, like compounds of the formula $PR^1R^2R^3$ or $P(OR^1) (OR^2) (OR^3)$, in which $R^1$, $R^2$ and $R^3$ represent aliphatic, aromatic or alkylaromatic hydrocarbon groups with 1-20 carbon atoms, and corresponding arsenic and antimony compounds. Examples are triethylphosphine, tributylphosphine, tri-cyclohexylphosphine, methyl diphenylphosphine, diethylphenylphosphine, triphenylphosphine, tri-p-toluylphosphine, trinaphtylphosphine, ethylene di-(dimethylphosphine), trimethylphosphite, trimethylolpropanephosphite, triphenylphosphite, triphenylarsine, phenyldimethylarsine, and triphenylstibine.

Suitable as carrier material are inorganic and organic, porous carrier materials, such as silicon, siliconalumina, alumina, zeolites, diatomaceous earth, active carbon, graphite, and porous macroreticular resins.

The carrier material may be applied in any form suitable for fixed-bed or fluid-bed operation, such as extrudates, pellets, cylinders and non-uniformly broken particles.

The pore volume of the carrier may amount to between 0.01 and 5 cm$^3$/gram. Preferably, macroporous carriers are applied and, in particular, carriers with a bimodal pore distribution, which means carriers having part of the pore volume in the range of pore diameters smaller than 100 Å and part in the range of pore diameters larger than 100 Å, preferably larger than 1000 Å. Pore volume is here understood to be the volume of pores with a pore diameter up to 20,000 Å as can be determined by nitrogen-capillary condensation for pores up to a pore diameter of approximately 1000 Å and by the mercury penetration method for pores having a pore diameter up to 20,000 Å.

The liquid load varies from 0.01 to 0.95 cm$^3$ of liquid/cm$^3$ of pore volume and more particularly between 0.1 and 0.8 cm$^3$ of liquid/cm$^3$ of pore volume. By liquid load is meant the part of the pore volume filled up with liquid or solid solution of the metallo-organic complex in free ligand. The liquid load will to a high degree be dependent of the type of carrier material applied and of the fact whether the ligand is applied in solid or liquid condition. In order to achieve as high as possible an utilization degree of the catalyst just such an amount of liquid will be impregnated, for instance in the case of a carrier with a bimodal pore distribution, that the micropores, i.e. the pores having a diameter smaller than 100 Å, are fully filled with liquid, while in the macropores only the walls are covered by a thin layer of liquid.

Transportation of reagents and products can then take place by means of diffusion in the macropores filled with gas. If the free ligand is solid under the reaction conditions, i.e. if a Supported Solid Phase Catalyst is used, a smaller load is preferably applied, for instance between 0.1 and 0.55 cm$^3$ of solution/cm$^3$ of pore volume, than in case of a Supported Liquid Phase Catalyst, the free ligand then being present in the liquid condition.

The concentration of the metallo-organic complex in the free ligand may vary between broad limits; the upper limit is determined by the solubility of the metallo-organic complex in the free ligand under the reaction conditions, the lower limit being mainly determined by economical and commercial considerations.

Hence, the range within which the concentration may vary amounts, for instance, to $10^{-1}$–$10^{-5}$ moles/liter.

In the preparation of the catalyst the carrier may be impregnated with a solution of the catalytically active metallic complex or a precursor thereof in free ligand without any other solvents. Just such an amount of solution is then used that the required loading degree is reached immediately.

However, it is easier to use an inert auxiliary solvent in the catalyst preparation, which means impregnating the carrier with a solution of the catalytically active metallic complex or a precursor thereof in a mixture of one or more free ligands and a volatile solvent, and removing the volatile solvent again thereafter.

Inert, volatile solvent is understood to mean a component which does not incur a strong coordination with the metallo-organic complex, which has a vapour pressure higher than the vapour pressure higher than the vapour pressure of the ligand by at least a factor ten, and which forms a homogeneous solution with the free ligand and the metallo-organic complex, such as methanol, ethanol, benzene, toluene, xylene.

If an initial complete saturation of the carrier material is intended, the ratio between free ligand and inert, volatile solvent is determined by the required loading degree of the catalyst. For instance, in order to obtain a loading of 0,5, just 50% of the catalyst solution obtained has to consist of volatile solvent. Just such an amount of catalyst solution is impregnated that, in the first instance, the entire pore volume of the carrier material becomes filled up. If the ligand is present at room temperature in the solidified state, the mixture consisting of metallo-organic complex, free ligand and inert volatile solvent, is heated to the temperature at which a homogeneous solution is obtained. The warm, homogeneous catalyst solution is slowly added to the carrier material, which is likewise warm, with exclusion of atmospheric oxygen and with stirring. The carrier material has previously been raised to a temperature which is at least equal to the temperature of the catalyst solution used. Also the impregnation may be carried out in vacuo. The resulting free-flowing catalyst is now stripped of the volatile solvent in vacuo, by inert gas being passed through or, in situ, in the reactor, at a temperature at which the volatile solvent evaporates and which lies above the melting temperature of the free ligand. In this way a possible re-distribution of the free ligand may take place in the carrier material already during the drying of the catalyst.

Unsaturated organic compounds that can be converted by the process according to the invention are terminal or internal linear or branched aliphatic mono-olefins with 2–20 carbon atoms, conjugated or non-conjugated diolefins with 4–20 carbon atoms, cycloaliphatic and aromatic olefins with 6–20 carbon atoms, olefinically unsaturated aldehydes with 3–20 carbon atoms and the acetals derived therefrom, olefinically unsaturated ketones with 4–20 carbon atoms and ketals derived therefrom, unsaturated esters and unsaturated nitriles. Examples are ethene, propene, butene-1, isobutene, butene-2, hexene-1, octene-1, octene-4, diisobutene, cyclohexene, styrene, butadiene, pentadiene 1–4, cycle-octadiene, acrolein, crotonaldehyde, cinnamaldehyde, 1.1 dimethoxy-propene-2, methylvinylketone, methylacrylate, methylmethacrylate, diethylmaleate, acrylonitrile. The process according to the invention is particularly suitable for hydroformylation of, among others, olefins, unsaturated aldehydes and acetals derived therefrom.

The reaction temperature may vary from 20°–300° C., depending on the free ligand, metallo-organic complex, olefin and total pressure applied. At too high a temperature the free ligand and the metallo-organic complex become volatized or decomposed; at too low a temperature the olefin or the formed aldehyde condenses in the reactor and the activity becomes too low. It also appeared that the temperature affected the selectivity, it becoming apparent that the selectivity—in the hydroformylation of propene at a total pressure of 16 atmospheres, with rhodiumhydridocarbonyltris (triphenylphosphine) dissolved in triphenylphosphine and impregnated on silicon-alumina for catalyst—becomes higher at a rising temperature. The preferred temperature amounts to 40°–200° C.

The total pressure may vary from 1–100 bar, depending on the olefin applied. By preference, the total pressure however amounts to 1 to 20 bar, seeing that at this low total pressure a high activity and selectivity and low investment costs can be realized.

It was found that the partial pressures of the respective components play an important part in the new process. For instance, in the hydroformylation of propene at 90° C. and a total pressure of 16 atmospheres with rhodium-hydridocarbonyltris (triphenylphosphine) dissolved in triphenylphosphine and impregnated on siliconalumina for catalyst it appeared that the selectivity and activity increase at a decrease of the partial pressure of the carbon monoxide. At a decrease of the carbon monoxide partial pressure from 5.3 to 1 at abs. the selectivity rose from 7 to 20 and the activity became larger by a factor 1.5. A molar ratio of CO to olefin of between 1:10 and 5:10 thus is advantageous in hydroformylation.

It was found that the pore structure of the carrier material may exert great influence on the activity for hydroformylation. For instance, in the hydroformylation of ethylene at 90° C. and a total pressure of 12 atmospheres with rhodiumhydridocarbonyltris (triphenylphosphine) dissolved in triphenylphosphine it was found that the activity of a catalyst having a carrier with a bimodal pore distribution with macro- and micro-pores for carrier material was eight times as high as the activity of a catalyst having only micro-pores in the carrier material.

It was found that said catalysts are also active at a reaction temperature below the melting point of the free ligand used, so that this concerns a 'Supported Solid Phase Catalyst'. Surprisingly, it then appeared that, proceeding from a reaction temperature at which the free ligand is liquid to a reaction temperature at which the free ligand is solidified, no abrupt decrease in activity was observed round the melting point of the free ligand. On the contrary, the course of the activity as a function of the time could, with application of macro-porous or bimodal carrier material, be described throughout the temperature range by the same activation energy according to the Arrhenius equation. In case of a micro-porous carrier material, with a strong diffusion-limitation occurring, the activation energy appeared to differ strongly above and below the melting point of the free ligand.

From a technological point of view this Supported Solid Phase Catalyst is highly interesting, since, with use of a volatile, free ligand, the reaction temperature can be decreased, while retaining a high activity, to a point below the melting point of the free ligand at which the free ligand no longer becomes volatized. Also, at this low temperature an embodiment will be possible in which the above-mentioned catalyst is applied in a three-phase system, which means that liquid olefin is passed over a fixed bed of catalyst together with hydrogen and carbon monoxide. It is a prerequisite that the metallo-organic complex and the free ligand do not become dissolved in the olefin and the product.

The susceptibility of the resulting catalysts to poisoning by oxygen appears to be slight. If about 90 ppm of oxygen is added to the reaction mixture, the activity—in the hydroformylation of ethylene at 90° C. and a total pressure of 12 atmospheres, with rhodiumhydridocarbonyltris (triphenylphosphine) dissolved in triphenylphosphine and impregnated in $\gamma$-alumina for catalyst—appears to decrease in 15 hours' time to 60% of the initial activity, whereupon the activity remains constant at this level. If a catalyst is prepared which is outside the scope of this invention, by dissolving rhodiumhydridocarbonyltris (triphenylphosphine) in dioctylphthalate with excess triphenylphosphine (P/Rh=50) and impregnated on silicon-alumina, the activity, under the influence of 90 ppm of $O_2$, appears to have decreased in 10 hours' time to 20% of the initial activity, whereupon this activity level is maintained for more than 40 hours.

The supported, liquid phase catalysts applied according to the invention have a satisfactory stability, activity and selectivity. However, upon the start of the reaction with fresh catalyst an initial period occurs during which the activity of the catalyst rises gradually. In certain cases, this initial period may amount to between 50 and 250 hours.

The process according to the invention can be improved by applying a catalyst with the catalytically active metallic complex being dissolved in a mixture of one or more ligand-forming compounds and one or more additives soluble or miscible in these compounds, which additives decrease the surface tension of the solution referred to the carrier material and/or referred to the gas phase in comparison with a solution without additive.

It has proved possible to shorten the initial period and even to increase the activity of the catalyst by application of these additives.

As additives are to be considered compounds which are soluble in, or miscible with, the ligand-forming compound acting as solvent to the catalytically active complex, and which compounds decrease the surface tension or, as the case may be, the interfacial tension of the solution with respect to the carrier material and/or with respect to the gas phase. Further, the additives should not be volatile, or have limited volatility and should not form irreversible complex compounds with the metal of the catalytically active complex.

Suitable additives are, among others, compounds from the group of polyetheneglycol, polypropyleneglycol, adducts of ethene oxide to aliphatic linear or branched alcohols with 1–30 carbon atoms, adducts of ethene oxide to alkylphenols with 7–30 carbon atoms, and ethene oxide propene oxide copolymers, and ionogenic surface-active compounds, such as alkylphenolether-sulphates and alkylsulphonates. Good results are already achieved with use of relatively low-molecular polyethyleneglycol having a molar weight of between 150 and 2500.

The additives may be applied in quantities of between 0.1 and 65% by weight referred to the quantity of additive and ligand-forming compound. By preference, however, a quantity of between 5 and 40% by weight is applied. Larger quantities lead to an appreciable decrease of the molar ratio between the ligand-forming compound and the transition metal, as a result of which the selectivity may decrease.

The invention will be elucidated in more detail with the aid of the following example, without being limited to these specific embodiments.

The behaviour of each of the catalysts obtained, with respect to hydroformulation of ethylene and propene, was observed for a long time in a continuous high-pressure flow arrangement during so-called long-duration experiments. It was found that the catalysts obtained show a relatively long initial period, during which the activity increases rapidly, whereupon the activity remains constant or keeps increasing slowly for a very long time. The course of the activity depends to some degree on the carrier material, solvent and olefin applied. For instance, in the hydroformylation of ethylene at 90° C. and a total pressure of 12 atm. with rhodiumhydridocarbonyltris (triphenylphosphine) dissolved in triphenylphosphine and impregnated on γ-alumina for catalyst, a constant activity was measured for more than 600 hours, whilst, with silicon-alumina for carrier material, the activity keeps increasing slowly for more than 600 hours.

EXAMPLE 1

Stabilizing action of a free ligand as solvent and the metallo-organic complex in the hydroformylation of ethylene.

With exclusion of air, 0.0183 of RhHCO(PPh$_3$)$_3$ was dissolved in 4.2 g of PPh$_3$ at 90° C. The resulting catalyst solution was slowly added to 9.1545 g of γ-Al$_2$O$_3$ 000-3P (AKZO-Chemie, Amsterdam, the Netherlands), with stirring and whilst nitrogen was passed through. The carrier material had been previously activated for 20 hours at 450° C. in vacuo. The particle diameter of the carrier material amounted to 0.42-0.50 mm, the average pore diameter to 45 Å, the pore volume of the activated carrier to 0.77 cm$^3$/g, and the pore volume amounted to 0.33 cm$^3$/g after impregnation with the catalyst solution. The pore volume and the average pore diameter were determined by means of N$_2$-capillary condensation according to the methods indicated by J. C. P. Brockhoff in 'Physical and Chemical Aspects of Adsorbents and Catalysts', Academic Press edition, London and New York, 1970, Chapter I. The resulting catalyst, coded SLPW-5, was tested for 600 hours in a continuous high-pressure flow arrangement for hydroformylation of ethylene at the following condition:

Temperature: 90° C.
Total pressure: 12 atm. ethylene
Composition: H$_2$/CO/ethylene=1/1/1
W/FC$_2$ (STP): 1.89 10$^{-3}$ (gRh)/ml of ethylene/s, in which W represents the weight of the rhodium already present in the reactor and FC$_2$=the number of ml of ethylene per seconds. For the results, see the table.

For the sake of comparison, the activity course of a catalyst beyond the scope of this invention was tested under identical reaction conditions. This concerns a catalyst coded PSA-38, described in Th.G. Spek, dissertation Delft 1976, in which Rh (π-allyl) CO (PPh$_3$)$_2$ was physisorbed in a mono-molecular layer on the surface of the pores of γ-Al$_2$O$_3$ 000-3P. The catalyst according to the invention, SLPW-5, had superior properties compared with PSA-38. For instance, for more than 600 hours SLPW-5 had a constant activity and, after 200 hours, the activity was 2.75 times as high as the activity of PSA-38. As the time advanced, this ratio became larger, seeing that PSA-38 kept becoming deactivated slowly, while SLPW-5 retained a constant activity. In this example, as well as in the next examples, the yield of aldehydes was invariably higher than 99% of the total amount of ethylene converted.

This example demonstrates the stabilizing effect of causing a metallo-organic complex to dissolve in a free ligand, and impregnated in the pore volume of a carrier material, with respect to the hydroformylation of ethylene.

EXAMPLE II

The influence of the carrier material on the activity for hydroformylation of ethylene and propylene.

Since the micro-porous catalyst SLPW-5 from example I showed a strong diffusion limitation (a larger particle diameter brought about a strong decrease in activity), a carrier material was tested which contained both macro- and micro-pores. For instance, 0.0260 g of RhHCO (PPh$_3$)$_3$ was dissolved at 60° C., with exclusion of air, in a solution consisting of 5.504 g of PPh$_3$ and 5.24 ml of benzene. The resulting homogeneous catalyst solution was slowly added—with stirring and whilst nitrogen was passed through—to 17,4728 g of silicon-alumina LA-30 (AKZO-Chemie, Amsterdam, the Netherlands), which had been activated in vacuo for 20 hours at 450° C. The particle radius amounted to 0.42-0.50 mm; the pore distribution was bimodal, with an average macro-pore radius of 4000 Å and micropores with an average radius of 55 Å; the pore volume amounted to 0.59 cm$^3$/g. After impregnation with the above-mentioned catalyst solution, the pore volume amounted to 0.27 cm$^3$/g, it appearing that the micropores were fully filled with catalyst solution and the walls of the macro-pores are covered by a thin layer of catalyst solution. After impregnation the catalyst, coded SLPW-9, was stripped of benzene for 20 hours at 90° C. by passage of nitrogen.

The resulting catalyst was tested in a continuous high-pressure flow arrangement for hydroformylation of ethylene at the following reaction conditions:

Temperature: 90° C.
Total pressure: 12 atm.
Composition: H$_2$/CO/CO$_2$==1/1/1
W/FC$_2$=(STP):SLPW-9 0.604.10$^{-3}$ (gRh).s/mlC$_2$=

The catalyst had an initial period of about 70 hours, following which the activity kept rising slowly for more than 500 hours.

After 500 hours the activity of SLPW-9 was eight times as high as the activity of SLPW-5 under comparable reaction conditions. Further see the table. SLPW-9 was also tested for hydroformylation of propene under the reaction conditions mentioned below.

Temperature: 90° C.
Total pressure: 16 atm.
Composition: H$_2$/CO/C$_3$==1/1/1
W/FC$_3$=(STP):0.972.10$^{-3}$ (gRh).s/ml C$_3$=

The initial period appeared to amount to about 20 hours, whereupon the activity kept increasing slowly for more than 400 hours, at a slower rate however than in the ethylene hydroformylation. The selectivity S, $$(S = \frac{\text{production of n-butyraldehyde}}{\text{production of iso-butyraldehyde}})$$

amounted to 7.4. throughout the activation period.

EXAMPLE III

The influence of the reaction temperature on the activity for hydroformylation of ethylene and propene.

The catalysts SLPW-5 and SLPW-9 mentioned in the examples I and II were started from. The influence of the temperature on the activity for hydroformylation of ethylene and propene was examined at the reaction conditions mentioned in the examples I and II, the reaction temperature varying from 65° C. to 120° C.

In the plotting of the ln (reactivity) against the reciprocal of the temperature in °K. two areas can be distinguished in case of micro-porous and diffusion-limited SLPW-5 in the hydroformylation of ethylene; below the melting point of triphenylphosphine (80° C.) the activation energy amounted to 16.39 kcal/mole and above this temperature to 5.92 kcal/mole. The activation energy for the macro-porous and non-diffusion-limited SLPW-9 amounted in the hydroformylation of ethylene under the reaction conditions mentioned in example II to 14.2 kcal/mole over the whole temperature range. When SLPW-9 was tested for hydroformylation of propene at the reaction conditions mentioned in example II the activation energy amounted to 18.7 kcal/mole over the whole temperature range.

In the above experiment the continuous course of the activity round the melting point of triphenylphosphine without any change of the activation energy was surprising.

This example demonstrates the high activity of both a Supported Solid Phase Catalyst and a Supported Liquid Phase Catalyst with respect to hydroformylation of olefins, and it demonstrates at the same time the influence of the pore structure of the carrier material on the course of the activity for hydroformylation as a function of the temperature.

EXAMPLE IV

The influence of the solvent on the activity for hydroformylation of ethylene and propene.

In order to make comparison possible with the catalyst disclosed in the British Patent Specification, 1,185,453 the following catalyst was prepared, outside the scope of the invention: 0.0235 g of RhHCO(PPh$_3$)$_3$ and 0.3245 g of PPh$_3$ were dissolved, with exclusion of air, at 60° C., in a solution of 3.9339 g of di-(octyl)-phthalate and 5.37 ml of benzene. The resulting homogeneous catalyst solution was slowly added—with stirring and whilst nitrogen was passed through—to 15.2017 g of the silicon-alumina, LA-30, mentioned in example II. The particle diameter amounted to 0.42–0.50 mm. The catalyst was stripped of benzene by passage nitrogen for 20 hours at 90° C.

The resulting catalyst, coded SLPW-10, was tested for hydroformylation of ethylene under the following reaction conditions:
Temperature: 90° C.
Total pressure: 12 atmospheres
Composition: H$_2$/CO/C$_2$= =1/1/1
W/FC$_2$=(STP):0.594 (gRH).s/mlC$_2$=

The activation course of SLPW-10 differed strongly from the activation course of a catalyst according to the invention, for instance SLPW-9. After 200 hours the activity of SLPW-10 was about 20% lower than that of SLPW-9. Catalyst SLPW-10 was also used for hydroformylation of propene at 90° C., a pressure of 16 ats abs., a catalyst load W/FC$_3$ of 0.91×10$^{-3}$, analogous to example II. After 160 hours the activity of this catalyst amounted to only 6% of the activity of the SLPW-9 catalyst according to the invention, while the selectivity amounted to only 2.3 to 2.6. Further see the table 1.

Table 1

| conditions | cat | activity in ml of olefin converted/gRh/sec. Time in hours | | | | | | | | |
|---|---|---|---|---|---|---|---|---|---|---|
| | | 20 | 40 | 80 | 120 | 160 | 200 | 280 | 400 | 500 |
| 1 | SLPW-5 | 12 | 14 | 16 | 18 | 18 | 18 | 18 | 18 | 18 |
| 2 | SLPW-9 | 36 | 70 | 101 | 111.5 | 118 | 124 | 133 | 150 | 164 |
| 3 | PSA-38* | 22 | 16 | 13 | 10 | 8 | 6.5 | — | — | — |
| 4 | SLPW-10* | 2.5 | 6 | 19 | 42 | 75 | 95 | — | — | — |
| 5 | SLPW-9 | 4.2 | 4.7 | 5.3 | 5.7 | 6.1 | 6.45 | 7.2 | — | — |
| 6 | SLPW-10* | nd | nd | 0.30 | 0.35 | 0.40 | nd | — | — | — |

*catalyst not according to the invention
nd = not determined

| conditions | T °C. | P ats abs. | W/C$_2$ | W/C$_3$ |
|---|---|---|---|---|
| 1 | 90 | 12 | 1.89 × 10$^{-3}$ | — |
| 2 | 90 | 12 | 0.604 × 10$^{-3}$ | — |
| 3 | 90 | 12 | 1.87 × 10$^{-3}$ | — |
| 4 | 90 | 12 | 0.594 × 10$^{-3}$ | — |
| 5 | 90 | 16 | — | 0.972 × 10$^{-3}$ |
| 6 | 90 | 16 | — | 0.910 × 10$^{-3}$ |

In all cases the molar olefin: CO:H$_2$ ratio was 1:1:1.

This example demonstrates the high activity and favourable activation course of a catalyst according to the invention compared with a known catalyst, the metallo-organic complex being dissolved in a high-boiling solvent other than the ligand itself.

EXAMPLE V

The influence of the reaction conditions on the selectivity in the hydroformylation of propene.

The influence of the reaction conditions on the selectivity was examined. To this end, in the hydroformylation of propene under the reaction conditions mentioned in example II, the temperature was varied from 70° C. to 118° C., with SLPW-9 for catalyst, in which, at a rise of the reaction temperature from 70° C. to 118° C., the selectivity rose from 6.0 to 9.5. The activation energy for formation of n-butyraldehyde amounts to 19.0 kcal/mole and for formation of iso-butyraldehyde to 16.5 kcal/mole. When the carbon monoxide partial pressure dropped from 5.33 atm. to 2.29 atm., at which the H$_2$CO/C$_3$= ratio decreased from 1/1/1 to 3/1/3, the selectivity rose from 7.4 to 11.5 and the activity from 7.4 to 12.5 mlC$_3$=/(gRh).s at a reaction temperature of 90° C. When the H$_2$/CO/C$_3$= ratio amounted to 3/1/1 or to 1/1/3, the selectivity at 90° C. was 9.4 in either case. This example demonstrates the favourable influence of a high reaction temperature and a low carbon monoxide partial pressure on the activity and the selectivity of a catalyst according to the invention.

EXAMPLE VI

A series of catalysts were prepared in the way described in example II. For carrier silica 000-3E (Akzo-Chemie, Amsterdam) was applied having a pore volume of 0.85 cm$^3$/g, a specific surface area of 186 m$^2$/g, and an average pore diameter of 67 Å. For catalytically active complex RhHCO (PPh$_3$)$_3$ was applied, dissolved in triphenylphosphine or in a mixture of triphenylphosphine and polyethyleneglycol having an average molar weight of 200, invariably in a concentration of 5.34 millimoles of rhodium-complex per liter of solvent. The loading degree of the pore system of each catalyst was 0.56.

The catalysts obtained this way were applied for hydroformylation of propene. The reaction was carried out in all cases at a pressure of 16 ats abs., a temperature of 90° C., a molar $H_2:CO:C_3H_6$ ratio of 1:1:1, a catalyst load $W/F_{c3}$ of $0.984 \times 10^{-3}$ gRh/ml of propene/S, and a supply of each of the reactants of 45 cm³ (NTP)/minute. The results are summarized in the following table 2.

Table 2

| test | solvent weight-% polyetheneglycol | initial period (hour) | reactivity cm³C₃/gRh/s | selectivity n/iso |
|---|---|---|---|---|
| 1 | 0 | 120 | 5.40 | 7.8 |
| 2 | 2.1 | 10 | 5.34 | 8.34 |
| 3 | 10.4 | 10 | 9.00 | 8.60 |
| 4 | 20.7 | 9 | 8.42 | 8.83 |
| 5 | 31.0 | 8 | 8.78 | 8.61 |
| 6 | 51.2 | 9 | 9.89 | 7.75 |

It appears that because of the presence of the polyethyleneglycol not only the initial period is strongly reduced, but also that the ultimate activity and selectivity of the catalyst improve. As far as the selectivity is concerned there is an optimum value lying at a quantity of additive of approximately 20 w.-%. Upon application of a quantity of additive of more than 40 w.-% the reactivity increases still further, but the selectivity drops distinctly.

Analogous results were obtained with use of silica D 11—11 (BASF) having a pore volume of 0.81 cm³/g, a specific surface area of 112 m²/g, and an average pore diameter of 149 Å.

When the polyethyleneglycol having an average molar weight of 200 was replaced by polyethyleneglycol with an average molar weight of 1000 the same reduction of the initial period was found. The reactivity and the selectivity, however, were only slightly higher. At 10 w.-% of this additive and silica 000-3E for carrier material, under the reaction conditions described above, the reactivity was 6.0 cm³ of propene/gRh/s at a selectivity of approximately 8.

EXAMPLE VII

A number of ligand-forming compounds were tested by preparing solutions of RhHCO (PPh₃)₃ in various ligand-forming compounds, in a concentration of 28.6 millimoles of complex per liter of ligand-forming compound. As carrier material diatomaceous earth (type MP-99 obtained from Eagle Pritchard Co, USA) was used, having a pore-voluem of 1.064 cm³/g for pores up to 20,000 Å, a specific surface of 16 m²/g, an average radius of the pores of 3200 Å and a particle size of between 0.42 and 0.50 mm. This carrier was impregnated as described in example II with the various solutions, so that catalysts with a loading factor of 0.43 were obtained.

These catalysts were used in the hydroformylation of propylene at 90° C., a total pressure of 16 ata, a total gas throughput of 45 cm³/minute, a propylene throughput of $0.985 \cdot 10^{-3}$ gRh/cm³ propylene/S and a $H_2:CO:C_3$ = ratio of 1:1:1. The results are gathered in table 3.

Table 3

| ligand-former | melting point °C. | activity cm³C₃=/gRh/S | selectivity n/iso |
|---|---|---|---|
| triphenylphosphine | 80 | 6.0 | 8.96 |
| tritolylphosphine | 147.4 | 3.8 | 5.50 |
| triphenylarsine | 60.5 | 1.4 | 3.41 |
| triphenylphosphine oxide | 156.5 | 1.1 | 2.22 |
| triphenylphosphite | 25 | 1.1 | 3.66 |

In the same way tritolylphosphite (melting point 131° C.) was tested as ligand-forming compound, however at a temperature of 140° C. instead of 90° C. The activity was 1.5 cm³C₃=/gRh/S and the selectivity was 5.75.

EXAMPLE VIII

Various carrier materials were tested by impregnation according to example II to a loading factor of 0.50 with a solution of RhHCO (PPh₃)₃, in triphenylphosphine in a concentration of 5.5 millimoles/l. The catalysts which were thus obtained were tested by using them for the hydroformylation of ethylene. The reaction conditions were: a temperature of 90° C., a total pressure of 12 ata, a gas throughput of 45 cm³/minute, an ethylene throughput corresponding to $0.570 \cdot 10^{-3}$ gRh/cm³C₂=/S and a $H_2:CO:C_2$ = ratio of 1:1:1.

The results are gathered in table 4.

Table 4

| carrier | pore-volume cm³/g | average pore radius, Å | specific surface m²/g | reactivity cm³C₂= gRh/S |
|---|---|---|---|---|
| Silica 000-3E (Akzo Chemie) | 0.91 | 67 | 186 | 239 |
| Silica D-11-11 (BASF AG) | 0.81 | 149 | 112 | 77 |
| Silicagel A | 0.86 | 36 | 431 | 60 |
| Silica-alumina LA 30 (Akzo Chemie) | 0.59 | 54 and 1800 | 156 | 150 |
| γ-alumina 005-075E Akzo Chemie) | 0.72 | 69 | 182 | 55 |
| γ-alumina 000-3P (Akzo Chemie) | 0.72 | 45 | 240 | 42 |
| Diatomaceous earth MP-99 (Eagle Pritchard Co) | 1.064 | 3200 | 16 | 186 |

We claim:

1. In a process for the hydroformylation of the olefinically unsaturated organic compound containing 2 to 20 carbon atoms to produce the corresponding aldehyde having an additional carbon atom by reaction of said compound with hydrogen and carbon monoxide at a temperature of between 20° C. and 300° C. and at a pressure of between 1 and 100 bar in the presence of a catalyst consisting of a solid, porous carrier in the pores of which a catalytically active metallo-organic complex, containing as the central metal atom at least one metal selected from the group consisting of rhodium, cobalt, ruthenium and iridium, dissolved in a solvent of low volatility under the reaction conditions, is present, the improvement comprising using a catalyst wherein said catalytically active metallo-organic complex is present in the pores of the carrier in the form of a solution in at least one ligand-forming electron-donating phosphorous compound with a vapor pressure of less than 15 mbar under the reaction conditions, having the formula $PR^1R^2R^3$ or $P(OR^1)(OR^2)(OR^3)$ in which $R^1$, $R^2$ and $R^3$, independent of each other, or together, represent a C1 to C20 hydrocarbon group, the concentration of the complex being between 0.1 to 0.00001 moles of complex per liter of solvent.

2. Process according to claims 1 or 3 wherein an organic or inorganic, porous solid is used as said carrier, a part of whose pore volume is formed by pores having a diameter less than 100 Å and part of the pore volume being formed by pores having a diameter greater than 100 Å.

3. Process according to claim 1, wherein the reaction is carried out at a temperature below the solidifying point of the solution of the metallic complex in the ligand-forming solvent.

4. Process according to claim 1 wherein the catalyst is used with the catalytically active metallo-organic complex dissolved in a mixture of at least one ligand-forming compound and at least one additive soluble or miscible in these compounds, which additive decreases the surface tension of the solution with respect to the carrier material, or with respect to the gas phase, or both in comparison with a solution without additive, the additive being present in an amount of between 0.1 and 65% by weight referred to the total amount of additive and ligand-forming compound.

5. Process according to claim 4 wherein the surface tension reducing additive is present in an amount of between 5 and 40% by weight.

6. Process according to claim 4 or 5 wherein the additive is selected from the group consisting of polyethyleneglycol, polypropylene-glycol, ethene oxide—propene oxide copolymers, addition products of ethene oxide to aliphatic alcohols with 1–30 carbon atoms, and addition products of ethene oxide to alkyl phenols with 7–30 carbon atoms.

7. Process according to claim 4 wherein the surface tension reducing additive is polyethyleneglycol having a molar weight of between 150 and 2500.

* * * * *